United States Patent [19]

Lin

[11] Patent Number: 5,520,688
[45] Date of Patent: May 28, 1996

[54] VERTEBRAL AUXILIARY FIXATION DEVICE

[76] Inventor: Chih-I Lin, 14292 Spring Vista La., Chino Hills, Calif. 91709

[21] Appl. No.: 277,765

[22] Filed: Jul. 20, 1994

[51] Int. Cl.⁶ .......................... A61B 17/70; A61B 17/86; A61B 17/68
[52] U.S. Cl. .......................... 606/61; 606/73; 606/60; 411/412
[58] Field of Search .......................... 606/61, 60, 72, 606/73, 53, 59; 403/343; 411/412, 413, 399

[56] References Cited

U.S. PATENT DOCUMENTS

| | | | |
|---|---|---|---|
| 4,877,364 | 10/1989 | Sorrentino | 411/412 |
| 5,196,014 | 3/1993 | Lin | 606/60 |
| 5,259,398 | 11/1993 | Vrespa | 606/73 |
| 5,306,275 | 4/1994 | Bryan | 606/60 |
| 5,325,226 | 10/1994 | Lin | 606/61 |

*Primary Examiner*—Stephen C. Pellegrino
*Assistant Examiner*—Scott Markow
*Attorney, Agent, or Firm*—Bacon & Thomas

[57] ABSTRACT

A vertebral auxiliary fixation device comprises an auxiliary fixation piece and a double-threaded self-locking screw. The auxiliary fixation piece has a coupling element located at one end thereof and a threaded through hole located at another end thereof. The screw is composed of a head, a second threaded portion engageable with the threaded through hole of the auxiliary fixation piece, and a first threaded portion intended to fasten onto a vertebra to be fixed or vertebrae contiguous to the vertebra. The vertebral auxiliary fixation device is employed in conjunction with a vertebra fixation device.

7 Claims, 3 Drawing Sheets

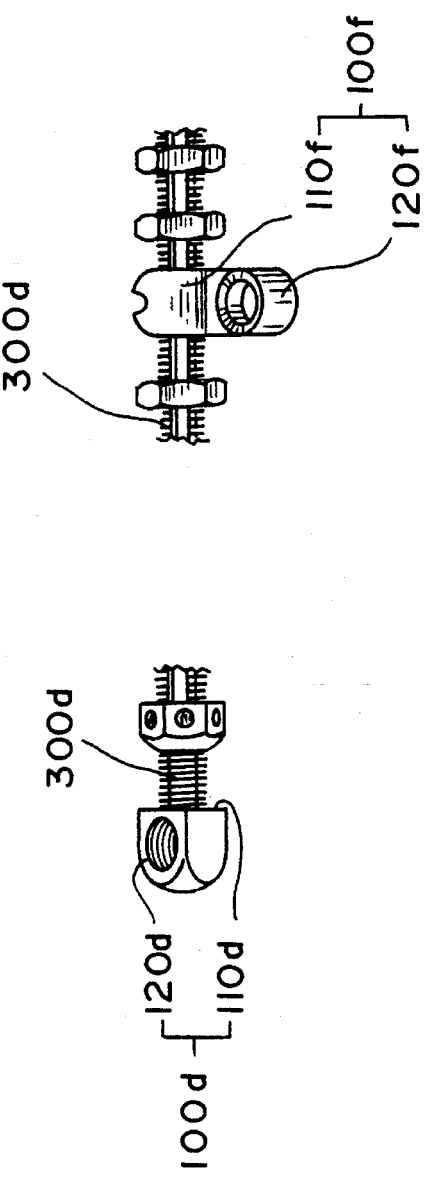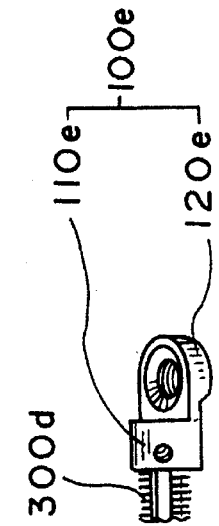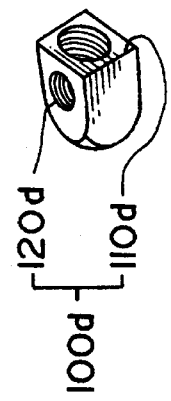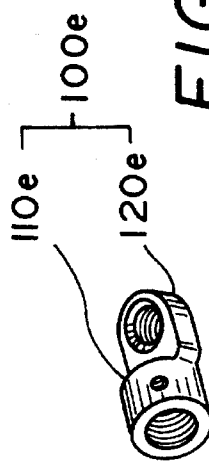

VERTEBRAL AUXILIARY FIXATION DEVICE

FIELD OF THE INVENTION

The present invention relates generally to a vertebral fixation device, and more particularly to a vertebral auxiliary fixation device.

BACKGROUND OF THE INVENTION

The conventional vertebral auxiliary fixation device is in fact a horizontal auxiliary fixation device. For example, fixing cords or clamping devices are used to connect two fixation rods of the vertebral fixation devices which are respectively fixed to a vertebra intended to be fixed and two vertebrae contiguous to the vertebra intended to be fixed. Such a horizontal auxiliary fixation device as described above is generally quite effective in fastening the fixation rods of two sets of vertebral fixation devices; nevertheless it is rather ineffective in providing an auxiliary effect of fixing the bone screws which are fastened onto a vertebra intended to be fixed or onto two vertebrae contiguous to the vertebra intended to be fixed. The above-mentioned horizontal auxiliary fixation device is similarly ineffective in providing an auxiliary effect of fixing the bone hooks which are used to hold a vertebra intended to be fixed or two vertebrae contiguous to the vertebra intended to be fixed. It is absolutely imperative that a vertebral auxiliary fixation device is employed to reinforce the fixation effect when a vertebral fixing and retrieving device is used to treat the deformed coccygeal vertebrae. The U.S. Pat. No. 5,133,717 discloses a coccygeal vertebrae fixing device comprising a plurality of auxiliary holes, each of which is dimensioned to receive therein an auxiliary bone screw. Such auxiliary holes as mentioned above are directly formed on the coccygeal vertebrae fixing device, thereby precluding a surgeon during an operation from choosing an appropriate vertebral auxiliary fixation device as required.

SUMMARY OF THE INVENTION

It is therefore the primary objective of the present invention to provide a vertebral auxiliary fixation device which is made up of an auxiliary fixation piece and a double-threaded self-locking screw.

The auxiliary fixation piece has one end serving as a coupling element for connecting the auxiliary fixation piece with a vertebral fixation device. Another end of the auxiliary fixation piece is provided with a threaded through hole.

The double-threaded self-locking screw comprises a head, a second threaded portion contiguous to the head, and a first threaded portion located at the posterior end of the double-threaded self-locking screw. The first threaded-portion is intended to be fastened onto a vertebra intended to be fixed or into one of two vertebrae contiguous to the vertebra intended to be fixed. The second threaded portion is intended to engage the threaded through hole of the auxiliary fixation piece. In the process of turning the double-threaded self-locking screw, the head of the screw is held securely by a fastening tool. In addition, the head of the double-threaded self-locking screw serves to stop the screw from moving through the threaded through hole of the auxiliary fixation piece.

Preferably, the coupling element and the threaded through hole of the auxiliary fixation piece of the present invention are made integrally.

The coupling element of the auxiliary fixation piece is coupled with a vertebral fixation device by any known method of the prior art, in which male and female threads, fitting means, or hooking means are generally involved. For example, if the present invention is used to attain an auxiliary fixation at the side wing of a vertebral fixation device, the coupling element of the auxiliary fixation piece is preferably a hooked element capable of catching and holding securely the fixation rod of a vertebral fixation device. If the present invention is used to accomplish an auxiliary fixation of the coccygeal vertebrae, the coupling element of the auxiliary fixation piece may be provided with male or female threads engageable with a threaded end of the fixation rod of the vertebral fixation device.

The threaded hole end of the auxiliary fixation piece of the present invention is provided with a threaded through hole engageable with the second threaded portion of the double threaded self-locking screw of the present invention. The threaded hole end of the auxiliary fixation piece may be circular, platelike, etc. in shape. For example, if the present invention is intended to achieve an auxiliary fixation of the coccygeal vertebrae, it is preferable that the threaded hole end of the auxiliary fixation piece has a circular shape, and the like. On the other hand, if the present invention is intended to attain an auxiliary fixation at the vertebral fixation device side wing, it is suggested that the threaded hole end of the auxiliary fixation piece has a platelike shape.

The threads of the first threaded portion of the double-threaded self-locking screw of the present invention are similar in construction to the threads of a bone screw which is used as a component part of an ordinary vertebral fixation device. However, the double-threaded self-locking screw of the present invention is characterized in that its second threaded portion has two to six, preferably two to four, intertwined threads which are spaced at a substantially equal distance, and each of the intertwined threads has a pitch substantially equal to the pitch of the first threaded portion of the double-threaded self-locking screw.

In order to achieve an excellent fastening effect, it is suggested that the threads of the first threaded portion of the double-threaded self-locking screw of the present invention should not be too small in size in view of the fact that the first threaded portion is intended to be fastened onto a vertebra to be fixed or onto vertebrae contiguous to the vertebra intended to be fixed. It is also recommended that the pitch of the second threaded portion of the double-threaded self-locking screw and the pitch of the threaded through hole of the auxiliary fixation piece should not be too large, because the threaded hole end of the auxiliary fixation piece has a rather limited thickness. It must be noted here that the pitch of the first threaded portion and the pitch of the second threaded portion of the double-threaded self-locking screw of the present invention must be identical to each other so as to ensure that an excellent fixation effect of the vertebral auxiliary fixation device of the present invention is attained as expected. If the pitch of the first threaded portion is greater than that of the second threaded portion, it is very likely that a vertebra to be fixed or the vertebrae contiguous to the vertebra will be damaged by the first threaded portion. Such a surgical mishap is brought about by the fact that the first threaded portion is fastened onto the vertebra at an advancing distance which is different from the advancing distance of the second threaded portion. Such a problem as described above becomes serious when the second threaded portion of the double-threaded self-locking screw begins engaging the threaded through hole of the auxiliary fixation piece even though the problem referred to above does not arise at the initial stage of the process of fastening the double-threaded self-locking screw onto the vertebra.

The second threaded portion of the double-threaded self-locking screw of the present invention has a plurality (n) of threads which are spaced equidistantly such that the distance between the corresponding points on two adjacent threads is 1/n of the original pitch. Similarly, the distance between the corresponding points on two adjacent threads of the threaded through hole of the auxiliary fixation piece is 1/n of the original pitch. Assuming that the pitch of the first threaded portion is 2.1 millimeters and that n is equal to 3, the distance between the corresponding points on two adjacent threads of the second threaded portion is 0.7 millimeter while the distance between the corresponding points on two adjacent threads of the threaded through hole is also 0.7 millimeter. However, the pitch is still 2.1 millimeters. As a result, the threaded hole end of the auxiliary fixation piece has a thickness which is more than sufficient to accommodate a plurality of threads so as to meet the technical requirements that the pitch of the first threaded portion is preferably large, and that the distance between the corresponding points on two adjacent threads of the second threaded portion is preferably small, and further that the first threaded portion and the second threaded portion are corresponding in the advancing distance (pitch) to each other.

The head of the double-threaded self-locking screw of the present invention is similar in construction to the head of a prior art bone screw, which may be hexagonal in shape.

The foregoing objectives, features, and advantages of the vertebral auxiliary fixation device of the present invention will be more readily understood upon a thoughtful deliberation of the following detailed description of the embodiments of the present invention in conjunction with the accompanying drawings.

BRIEF DESCRIPTION OF THE DRAWINGS

FIG. 5 illustrates a fourth auxiliary fixation piece constructed in accordance with the present invention coupled with a vertebral fixation rod.

FIG. 5a is a perspective view of the auxiliary fixation piece of FIG. 5.

FIG. 6 is a schematic view of a fifth auxiliary fixation piece constructed in accordance with the present invention shown coupled to a vertebral fixation rod.

FIG. 6a is a perspective view of the auxiliary fixation piece of FIG. 6.

FIG. 7 is a schematic view of a sixth auxiliary fixation piece constructed in accordance with the present invention coupled with a vertebral fixation rod.

DETAILED DESCRIPTION OF THE INVENTION

Figure 1:
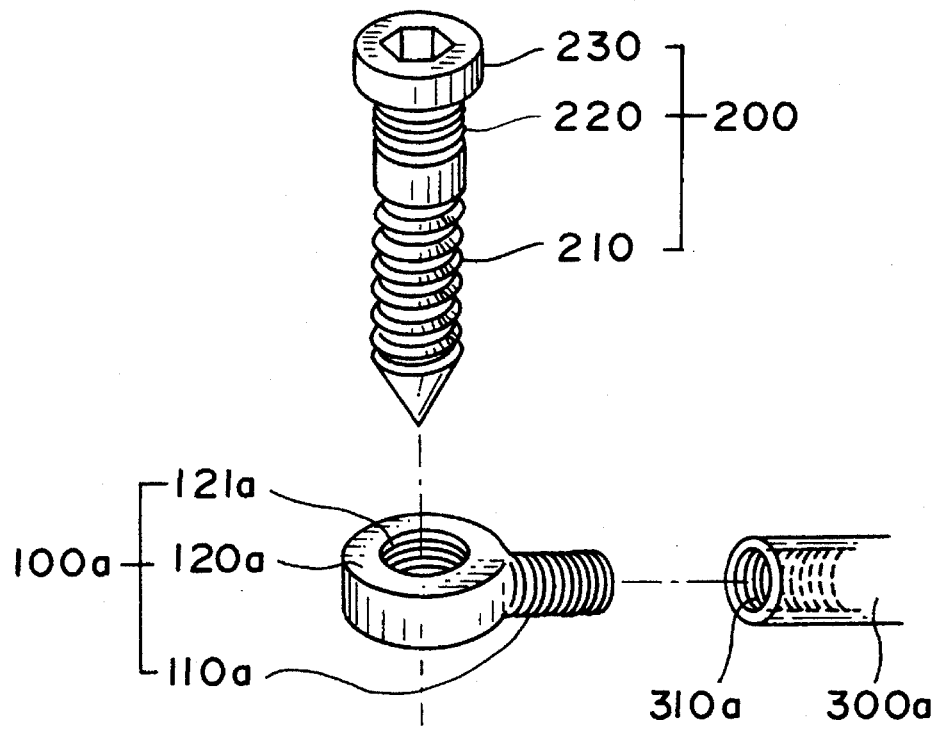
FIG. 1 shows an exploded view of a preferred embodiment of the present invention.

As shown in FIG. 1, a vertebral auxiliary fixation device of the first preferred embodiment of the present invention comprises an auxiliary fixation piece 100a and a double-threaded self-locking screw 200. The auxiliary fixation piece 100a is made up of a coupling element 110a, a threaded hole end 120a, and a threaded hole 121a. The double-threaded self-locking screw 200 comprises a head 230, a second threaded portion 220 adjacent to the head 230, and a first threaded portion 210 spaced from the head 230. The coupling element 110a of the auxiliary fixation piece 100a is so threaded that it is engageable with a threaded hole 310a of the fixation rod 300a of the vertebral fixation device.

Figure 2:
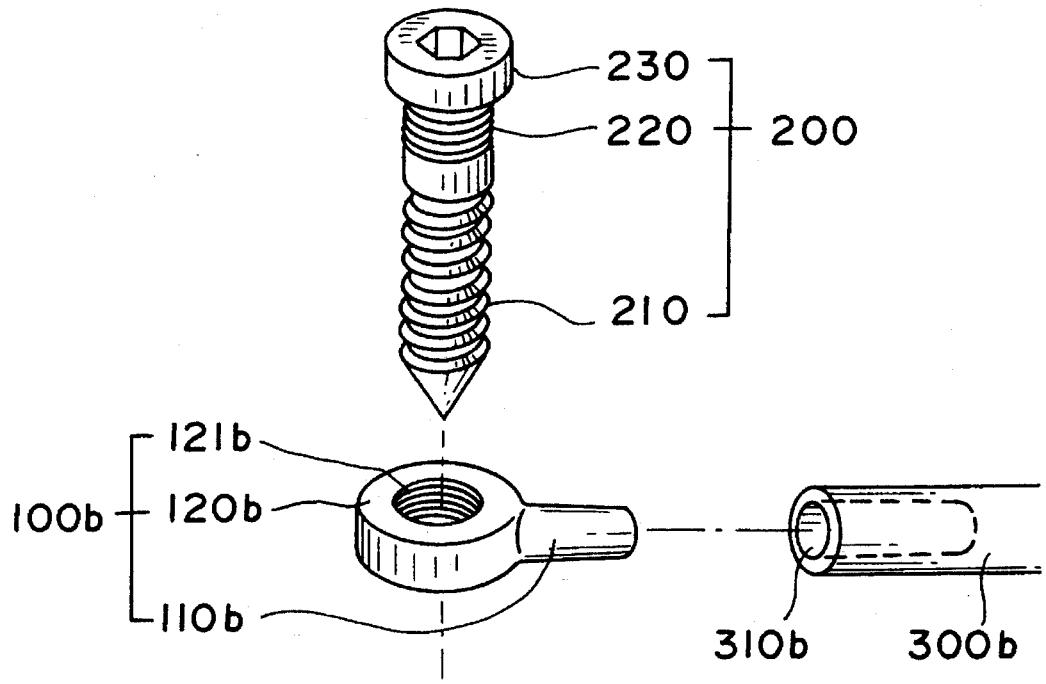
FIG. 2 shows an exploded view of another preferred embodiment of the present invention.

A vertebral auxiliary fixation device of the second preferred embodiment of the present invention is shown in FIG. 2 in which the reference numerals are similar in definition to the like reference numerals of FIG. 1. The second preferred embodiment of the present invention is different from the first preferred embodiment of the present invention in that the former has a coupling element 110b devoid of threads, and that the coupling hole 310b of the fixation rod 300b is also devoid of threads. In other words, the coupling element 110b is so dimensioned as to fit into the coupling hole 310b of the fixation rod 300b.

Figure 3:
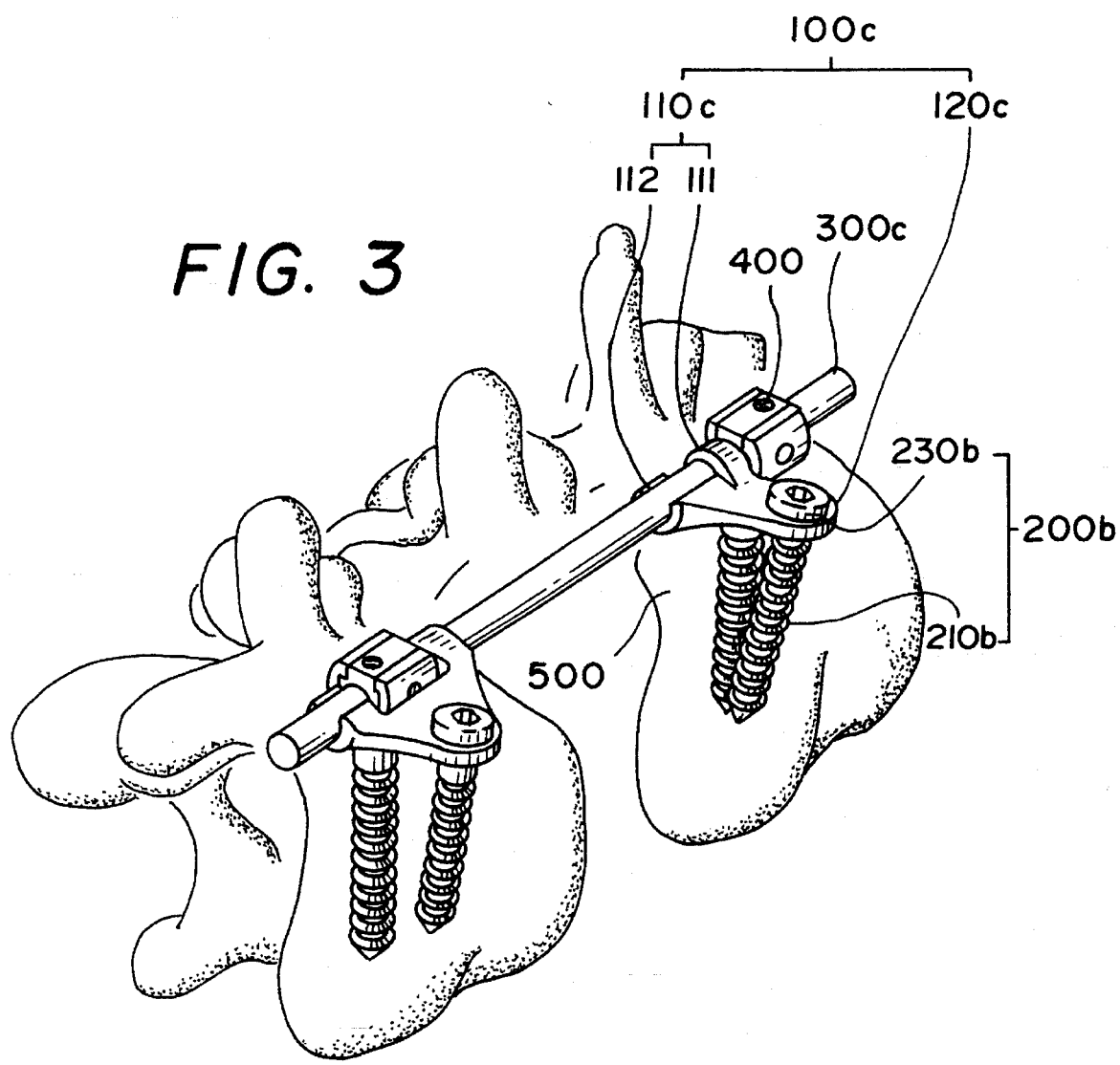
FIG. 3 shows a schematic view of still another preferred embodiment at work according to the present invention.
Figure 4:
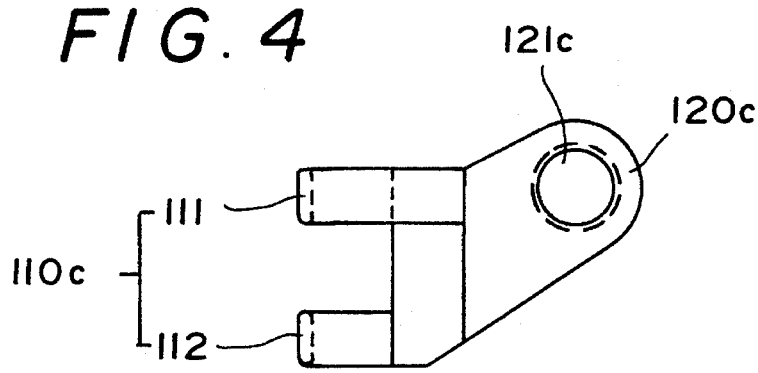
FIG. 4 shows a top plan view of the auxiliary fixation piece of the vertebral auxiliary fixation device as shown in FIG. 3.

The third preferred embodiment of the present invention is schematically shown in FIG. 3 in which the reference numerals are similar in definition to the like reference numerals of FIG. 1. The vertebral auxiliary fixation device of the present invention is employed in conjunction with a vertebral fixation device 400 intended to fix a deformed vertebra 500. The third preferred embodiment of the present invention comprises a coupling element 110c having two hooking pieces 111 and 112 which are capable of catching and holding the fixation rod 300c. As shown in FIG. 4, the auxiliary fixation piece 100c of the third preferred embodiment comprises a threaded hole end 120c having a threaded hole 121c.

The auxiliary fixation piece 100 of the present invention may be threadably coupled with the fixation rod in various forms, as illustrated in FIGS. 5–7 in which the reference numerals 100d, 110d, 120d and 300d are similar in definition to the like reference numerals of FIG. 1. As shown in FIGS. 5 and 6, the auxiliary fixation pieces 100d and 100e are threadably coupled with the externally threaded fixation rods 300d by means of a threaded hole (not shown in the drawings). On the other hand, the auxiliary fixation piece 100f is shown to be coupled with the fixation rod 300d by means of a hooking piece, having a central, threaded through bore (not shown) in FIG. 7.

What is claim is:

1. A vertebral auxiliary fixation device comprising:

an auxiliary fixation piece having a coupling element located at a first end thereof, said coupling element being removably attached to a vertebral fixation device with said coupling element being rotatable relative to said vertebral fixation device about a longitudinal axis defined by said vertebral fixation device, said auxiliary fixation piece further having a second end thereof provided with a threaded through hole; and a double-threaded self-locking screw having a head located at a top thereof, a second threaded portion adjacent to said head, and a first threaded portion spaced from said head for fastening said screw onto a vertebra, said second threaded portion being threadably engaged with said threaded through hole of said auxiliary fixation piece, said head being sized larger than said threaded through hole, said second threaded portion of said double-threaded self-locking screw including a plurality of intertwined threads; each of which has a pitch substantially equal to that of the threads of said first threaded portion of said screw.

2. The vertebral auxiliary fixation device according to claim 1 wherein said auxiliary fixation piece is circular in shape for fixing coccygeal vertebrae.

3. The vertebral auxiliary fixation device according to claim 1 wherein said second threaded portion comprises 2-4 intertwined threads which are equidistantly distributed.

4. A vertebral auxiliary fixation device comprising:

an auxiliary fixation piece having a coupling element located at a first end thereof, said coupling element being removably attached to a vertebral fixation device with said coupling element being rotatable relative to said vertebral fixation device about a longitudinal axis defined by said vertebral fixation device, said auxiliary fixation piece further having a second end thereof provided with a threaded through hole, wherein said coupling element comprises an externally threaded shaft that is threadably received within a threaded bore formed in an end of the vertebral fixation device; and a double-threaded self-locking screw having a head located at a top thereof; a second threaded portion adjacent to said head, and a first threaded portion spaced from said head for fastening said screw onto a vertebra, said second threaded portion being threadably engaged with said threaded through hole of said auxiliary fixation piece, said head being sized larger than said threaded through hole.

5. A vertebral auxiliary fixation device comprising:

an auxiliary fixation piece having a coupling element located at a first end thereof, said coupling element being removably attached to a vertebral rod-shaped fixation device with said coupling element being rotatable relative to said vertebral fixation device about a longitudinal axis defined by said vertebral fixation device, said auxiliary fixation piece further having a second end thereof provided with a threaded through hole, wherein said coupling element comprises a shaft that projects away from and tapers away from the second end of said auxiliary fixation piece, said shaft being received within an internal, tapering bore formed in an end of the vertebral fixation device; and a double-threaded self-locking screw having a head located at a top thereof, a second threaded portion adjacent to said head, and a first threaded portion spaced from said head for fastening said screw onto a vertebra, said second threaded portion being threadably engaged with said threaded through hole of said auxiliary fixation piece, said head being sized larger than said threaded through hole.

6. A vertebral auxiliary fixation device comprising:

an auxiliary fixation piece having a coupling element located at a first end thereof, said coupling element being removably attached to a vertebral fixation device with said coupling element being rotatable relative to said vertebral fixation device about a longitudinal axis defined by said vertebral fixation device, said auxiliary fixation piece further having a second end thereof provided with a threaded through hole, wherein said coupling element comprises a threaded hole which threadably receives the vertebral fixation device; and a double-threaded self-locking screw having a head located at a top thereof, a second threaded portion adjacent to said head, and a first threaded portion spaced from said head for fastening said screw onto a vertebra, said second threaded portion being threadably engaged with said threaded through hole of said auxiliary fixation piece, said head being sized larger than said threaded through hole.

7. A vertebral auxiliary fixation device comprising:

an auxiliary fixation piece having a coupling element located at a first end thereof, said coupling element being removably attached to a vertebral fixation device with said coupling element being rotatable relative to said vertebral fixation device about a longitudinal axis defined by said vertebral fixation device, said auxiliary fixation piece further having a second end thereof provided with a threaded through hole, wherein said coupling element comprises two hooking pieces which are rotatably attached to the vertebral fixation device at spaced locations along the longitudinal axis of the vertebral fixation device; and a double-threaded self-locking screw having a head located at a top thereof, a second threaded portion adjacent to said head, and a first threaded portion spaced from said head for fastening said screw onto a vertebra, said second threaded portion being threadably engaged with said threaded through hole of said auxiliary fixation piece, said head being sized larger than said threaded through hole.

* * * * *